(12) United States Patent
Dreher

(10) Patent No.: US 7,189,267 B2
(45) Date of Patent: Mar. 13, 2007

(54) OXYETHYLENATED BASED HAIR PRE-TREATMENT ANTI-PENETRATION COMPOSITION AND METHOD USING SUCH A COMPOSITION FOR LIMITING THE PENETRATION OF DYES INTO THE SKIN

(75) Inventor: Frank Dreher, Paris (FR)

(73) Assignee: L'Oreal, Paris (FR)

( * ) Notice: Subject to any disclaimer, the term of this patent is extended or adjusted under 35 U.S.C. 154(b) by 145 days.

(21) Appl. No.: 10/671,499

(22) Filed: Sep. 29, 2003

(65) Prior Publication Data

US 2004/0231071 A1 Nov. 25, 2004

Related U.S. Application Data

(60) Provisional application No. 60/416,963, filed on Oct. 9, 2002.

(30) Foreign Application Priority Data

Sep. 27, 2002 (FR) .................. 02 12032

(51) Int. Cl.
*A61K 7/13* (2006.01)
(52) U.S. Cl. .............. 8/405; 8/406; 8/410; 8/421; 8/552; 424/70.2; 424/70.6; 424/70.11; 132/202; 132/208

(58) Field of Classification Search ............... 8/405, 8/406, 410, 411, 421, 552; 424/70.2, 70.6, 424/70.11; 132/202, 208
See application file for complete search history.

(56) References Cited

U.S. PATENT DOCUMENTS

| 3,933,422 A | | 1/1976 | Saad .................... 8/10.1 |
| 5,500,218 A | * | 3/1996 | Kischka et al. ........... 424/401 |
| 5,527,832 A | * | 6/1996 | Chi et al. ............... 514/772.4 |
| 5,534,245 A | | 7/1996 | Galleguillos et al. ........ 424/66 |
| 6,235,273 B1 | | 5/2001 | Mackey .................. 424/63 |

FOREIGN PATENT DOCUMENTS

| DE | 102 00 185 | 7/2002 |
| EP | 0 801 942 | 10/1997 |

* cited by examiner

*Primary Examiner*—Eisa Elhilo
(74) *Attorney, Agent, or Firm*—Oblon, Spivak, McClelland, Maier & Neustadt, P.C.

(57) ABSTRACT

The present invention generally relates to a hair pre-treatment anti-penetration composition comprising an efficient amount of at least one oxyethylenated copolymer. The invention also relates to a method for limiting the penetration into the skin and/or the keratin fibres of at least one dye, contained in a hair dyeing composition, involving the pre-treatment application on the hair of such an anti-penetration composition, before the hair dye process.

71 Claims, No Drawings

OXYETHYLENATED BASED HAIR PRE-TREATMENT ANTI-PENETRATION COMPOSITION AND METHOD USING SUCH A COMPOSITION FOR LIMITING THE PENETRATION OF DYES INTO THE SKIN

The present invention generally relates to a hair pre-treatment anti-penetration composition comprising an efficient amount of at least one oxyethylene copolymer.

The invention also relates to a method for limiting the penetration into the skin and/or the keratin fibres of at least one dye, in particular an oxidation dye, contained in a hair dyeing composition, involving the pre-treatment application on the hair of an anti-penetration composition, before the hair dyeing process.

Some dyes, in particular some oxidation dyes, are able to cause discomfort, irritation, sensitization or staining reactions of the hair scalp, even if all the precautions are being taken during a dyeing operation in order to avoid any skin contact, if the opportunity to come in contact with the skin is very short, and if they are rinsed away just after the dyeing operation. Such intolerance reactions are triggered when the dye reaches or goes beyond the skin barrier.

For hair dyes able to cause such reactions, a limitation of the transcutaneous passage would result in a better tolerance towards the dye and would make it possible to prevent the skin from being stained.

Numerous compound families are known having the property to increase the penetration into the skin or the keratin fibres of an active ingredient contained in a cosmetic and/or pharmaceutical composition.

On the other hand, very little compound families are known having the opposite activity, i.e. efficiently reducing the penetration of an ingredient of a cosmetic and/or pharmaceutical composition into the skin and/or the keratin fibres.

It would be desirable to have compounds or formulations having reducing properties for the penetration into the skin and/or the keratin fibres of ingredients of cosmetic and/or pharmaceutical compositions.

Indeed, for some cosmetic formulations for application on the skin and/or the keratin fibres, it would be desirable to reduce, delay, or even prevent the ingredient penetration into the skin and/or the keratin fibres.

It would therefore be desirable to provide an agent which, when used as a complement of a basic cosmetic and/or pharmaceutical composition containing at least one cosmetically and/or therapeutically active agent, limits, or even prevents the penetration into the skin and/or the keratin fibres of the cosmetically and/or therapeutically active agent.

In particular, in the case of a hair dyeing operation, it would be desirable to have an agent, which, when used as a complement of a dyeing cosmetic composition for keratin fibres, for example hair, would limit, or even prevent the cutaneous absorption and the transcutaneous passage of the dye without adversely affect the keratin fibres coloration.

The Applicant has now found out that it was possible to limit the cutaneous absorption and the transcutaneous passage of dyes, more particularly of oxidation dyes, contained in a hair dye composition, in particular paraphenylene diamines, by applying as a pre-treatment on the hair scalp as well as on the hair before the dyeing composition is applied, a polymer based anti-penetration composition comprising oxyethylene functions.

In particular, the Applicant has found out that using at least one oxyethylene polymer selected amongst the polyethylene glycols comprising a average number of ethylene oxide groups higher than 45 and lower than 795, i.e., having a molecular mass higher than 2000 g.mol$^{-1}$ and lower than 35,000 g.mol$^{-1}$, the block polymers with ethylene oxide and propylene oxide blocks comprising more than 75 successive ethylene oxide groups in the chain per molcule and the polyethylene glycol copolymer comprising eight successive ethylene oxide and dicyclohexylmethane diisocyanate, groups would allow to limit the transcutaneous passage for dyes, more particularly oxidation dyes, contained in a hair dyeing composition.

The man of the art knows the use of oxyethylene polymers as anti-penetration agents in cosmetic compositions containing at least one active ingredient, with a view to limiting, or even preventing the active ingredient penetration into the skin.

Numerous scientific articles, as well as patents and patent applications disclose the anti-penetration effects of such polymers. For example, by way of an illustrative document, the publications J. Pharm. Sci. 67 (1978), 517–520; J. Pharm. Sci. 68 (1979), 596–598; and J. Controlled Release 23 (1993), 247–260, can be mentioned.

Also are included U.S. Pat. No. 5,650,171 and U.S. Pat. No. 5,700,483 which disclose topic compositions containing an efficient amount of retinoic acid as an active ingredient for treating the skin and a polyurethane with a high molecular mass (ranging up to 60,000 for U.S. Pat. No. 5,650,171 and up to 200,000 for U.S. Pat. No. 5,700,483) for reducing the retinoic acid transcutaneous passage; U.S. Pat. No. 5,989,527 which discloses topic compositions intended to be applied to the stratum corneum, containing an exfoliating active ingredient (such as for example an exfoliating chemical agent, a selftanning agent, a lightening agent for the skin and/or a insect-repellent agent) and a polyester for keeping the active ingredient in the stratum corneum thus preventing its transcutaneous passage; U.S. Pat. No. 5,833,961 disclosing water- and sweat-resistant sun compositions, containing at least two organic sunscreens as active ingredients and functionalized polyesters for fixing and maintaining the active ingredients in the stratum corneum; U.S. Pat. No. 4,938,951 which discloses topic liquid compositions, containing a topic active ingredient (such as for example a UV light absorbing agent, an insecticide, a pesticide, antimicrobial agents, fungicides or germicides, vitamins etc.), a volatile solvent and a film-forming polymer in solution in said solvent, said polymer being optionally selected amongst polyethylene glycol and propylene glycol and having the effect to improve the efficiency of a given active ingredient amount.

However, all those documents only relate co-formulation of such oxyethylene polymers with an active ingredient.

In addition, nothing is mentioned in those documents regarding the use of such polymers in hair dyeing compositions containing dyes, in particular oxidation dyes, for limiting the penetration thereof into the skin.

Moreover, it is known to the man of the art to use oxyethylene polymers in pre-treatment compositions for the skin or the hair scalp, intended to be applied as a pre-treatment before a cosmetic composition is applied onto the skin or a hair composition is applied onto the hair.

U.S. Pat. No. 6,001,377 may also be mentioned, disclosing skin care compositions and a method for improving the skin aspect, said compositions containing mineral particles (such as titanium oxide, zinc oxide, etc) and an oxyethylene polymer such as a polyethylene glycol; and U.S. Pat. No. 2,449,070 disclosing a protective coating for protecting the hands before the manicure, based on a cellulose derivate, a volatile solvent (such as ethanol), an emollient or a material under the form of a wax such as polyethylene glycol with an average molcular mass of 1,000 g.mol$^{-1}$ and polyethylene glycol with an average molcular mass of 1,500 g.mol$^{-1}$.

As far as, more particularly, the pre-treatment compositions to be applied on a hair scalp before a hair treatment are concerned, U.S. Pat. No. 4,592,908 can be mentioned disclosing a pre-treatment cream to be applied with a uncurling process in order to protect the hair scalp, containing vaseline, a $C_8$–$C_{18}$ oxyethylene fatty alcohol or an oxyethylene alkylphenol comprising 2 to 30 ethylene oxide groups, as well as an organic acid (or one of its saponifiable esters); U.S. Pat. No. 5,500,218 and International Application WO 93/16678 disclosing hair compositions to avoid the skin colouration and to protect the skin during a hair dyeing process, containing 27 to 50% in weight of polyethylene glycol with an average molcular weight ranging from 2,700 to 7,500 g.mol$^{-1}$; and finally, U.S. Pat. No. 4,545,978 disclosing a method for dyeing the hair involving the protection of the hair scalp, comprising the use of mineral substances having absorbing and filtering properties, such as, for example, active carbon, preferably in the form of suspension in a polyethylene glycol.

None of those documents discloses the use, in hair pre-treatment compositions to be applied on the hair scalp as well as on the hair before a dyeing composition containing dyes is applied, in particular oxidation dyes, of an oxyethylene polymer selected amongst polyethylene glycols with an average molcular mass higher than 2,000 g.mol$^{-1}$ and lower than 35,000 g.mol$^{-1}$, the block polymers with ethylene oxide and propylene oxide blocks comprising more than 75 successive ethylene oxide groups in the chain per molecule, and the polyethylene glycol copolymer comprising eight successive ethylene oxide and dicyclohexylmethane diisocyanate groups.

An object of the invention is therefore a hair pre-treatment anti-penetration composition comprising, in a physiologically acceptable medium, of an efficient amount higher than 5% in weight based on the total volume of the composition, at least one oxyethylene polymer selected amongst the group comprising:

a) polyethylene glycols with the general formula (1):

$$H(OCH_2CH_2)_nOH \quad (1)$$

where n is higher than 45 and lower than 795, b) block polymers with ethylene oxide and propylene oxide blocks, having the formula (2):

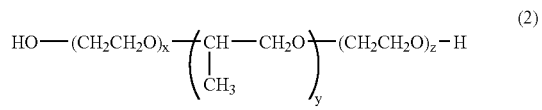

$$HO-(CH_2CH_2O)_x-\left(CH(CH_3)-CH_2O\right)_y-(CH_2CH_2O)_z-H \quad (2)$$

where x and z are such that at least one of x and z is higher than 75, and y is higher than 30, c) polyethylene glycol copolymer comprising 8 successive ethylene oxide and dicyclohexylmethane diisocyanate groups having the formula (3):

$$HO[(C_2H_4O)_8-(C_{15}H_{24}N_2O_2)-(C_2H_4O)_8]_xH \quad (3)$$

where x ranges from 1 to 4 such that the average mass of the copolymer is 1,800 g.mol$^{-1}$, d) mixtures of two or more of the compounds a), b) and c).

Advantageously, the oxyethylene polymer amount in the composition of the invention is lower than 20% in weight, preferably lower than 15% in weight, and more preferably, in the order of 10% in weight based on the total volume of the composition.

Advantageously, the polyethylene glycol a) having the formula (1) comprises 75 to 600 ethylene oxide groups per molecule.

Preferred polyethylene glycol examples include:

PEG-90 polyethylene glycol, comprising an average number of ethylene glycol groups of 90 and having a theoretical average molecular mass Mth of approximately 4,000 g.mol$^{-1}$, PEG-100 polyethylene glycol, comprising an average number of ethylene glycol groups of 100 and having a theoretical average molecular mass Mth of approximately 4,400 g.mol$^{-1}$, PEG-135 polyethylene glycol, comprising an average number of ethylene glycol groups of 135 and having a theoretical average molecular mass Mth of approximately 6000 g.mol$^{-1}$, PEG-150 polyethylene glycol, comprising an average number of ethylene glycol groups of 150 and having a theoretical average molecular mass Mth of approximately 6,600 g.mol$^{-1}$, PEG-180 polyethylene glycol, comprising an average number of ethylene glycol groups of 180 and having a theoretical average molecular mass Mth of approximately 7,900 g.mol$^{-1}$, PEG-200 polyethylene glycol, comprising an average number of ethylene glycol groups of 200 and having a theoretical average molecular mass Mth of approximately 8,800 g.mol$^{-1}$, PEG-240 polyethylene glycol, comprising an average number of ethylene glycol groups of 240 and having a theoretical average molecular mass Mth of approximately 10,600 g.mol$^{-1}$, PEG-350 polyethylene glycol, comprising an average number of ethylene glycol groups of 350 and having a theoretical average molecular mass Mth of approximately 15,400 g.mol$^{-1}$, PEG-454 polyethylene glycol, comprising an average number of ethylene glycol groups of 454 and having a theoretical average molecular mass Mth of approximately 20,000 g.mol$^{-1}$, the theoretical average molecular mass of a polyethylene glycol being calculated according to the equation (I):

$$Mth=18+44\times n \quad (I)$$

where n is as previously defined.

As examples of commercially available PEG-90, one can mention those marketed under the trade names:

Lipoxol 4000 MED from Condea Chimie,
Lutrol E-4000 Prill from BASF,
Macrogol 4000 from NOF,
Polyglycol E-4000 from DOW CHEMICAL,
Polyglykol 4000 from Clariant GmbH,
Unipeg-4000× from Universal Preserv-A-Chem,
Carbowax 4000 from Union Carbide,
Polyethylene glycol 4000 from FLUKA.

As examples of commercially available PEG-100, one can mention those marketed under the trade names:

CARBOWAX PEG 4600 (UNION CARBIDE),
Polyglycol E-4500 (DOW CHEMICAL).

As examples of commercially available PEG-135, one can mention those marketed under the trade names:
Lipoxol 6000 MED (Condea Chemie)
Macrogol 6000 (NOF).

As examples of commercially available PEG-150, one can mention those marketed under the trade names:
Lutrol E 6000 Prill (BASF)
Pluracol E 8000 (BASF)
Renex PEG 6000 (Uniqema Americas)
Sabopeg 6000 (Sabo)
Unipeg-6000× (Universal Preserv-A-Chem).

As examples of commercially available PEG-180, one can mention those marketed under the trade names:
Calgene PEG 8000 (Calgene)
CARBOWAX PEG 8000 (UNION CARBIDE)
Polyglycol E-8000 (DOW CHEMICAL)
Polyglykol 8000 (Clariant mbH)
Renex PEG 8000 (UNIQEMA AMERICAS)
Upiwax 8000 (UNIVERSAL PRESERV-A-Chem).

As examples of commercially available PEG-200, one can mention those marketed under the trade names:
Germinol (Dr. Gerhard Steidl)
Harmonic ASP (Dr. Gerhard Steidl)
Hexatrate Al-Free (Vevy)
Jonat AS (Dr. Gerhard Steidl).

As examples of commercially available PEG-240, one can mention those marketed under the trade names:
Lipoxol 12000 (Condea Chemie)
Polyglykol 12000 (Clariant GmbH).

As examples of commercially available PEG-350, one can mention those marketed under the trade names:
Lipoxol 20000 (Condea Chemie)
Polyglykol 20000 (Clariant GmbH)
Upiwax 20000 (Universal Preserv-A-Chem).

As examples of commercially available PEG-454, one can mention that marketed by FLUKA under the trade name Polyethylene glycol 20 000.

Advantageously, in the case of block oxyethylene polymers with ethylene oxide and propylene oxide blocks b) having the formula (2), the numbers x and z are such that at least one from x and z is equal to or higher than 80 and y is higher than 45.

As an example of a preferred block polymer, one can mention Poloxamer 407 (CTFA name) commercialized under the name Lutrol F-127® by BASF. In such a case, x and z are equal to 98 and y is equal to 67.

As an example of the block polymer, one can also mention:
Poloxamer 288 commercialized under the trades names Calgene Nonionic 1098-F (Calgene) and Pluronic F-98 (BASF),
Poloxamer 338 commercialized under the trades names Calgene Nonionic 1108-F (Calgene), Pluracare/Pluronic F-108 (BASF), Synperonic PE/F108 (Uniqema Americas).

As an example of the polyethylene glycol copolymer comprising eight successive ethylene oxide and saturated methylene diphenyldiisocyanate groups, one can mention that commercialized under the trade name Polyolprepolymer-15® (or PP-15®) distributed in France by Sederma.

The physiologically acceptable medium is a liquid medium that does not adversely affect the reducing effect of the absorption and of the transcutaneous passage of the oxyethylene polymer(s) useful according to the invention, nor the colouring property of dyes, including oxidation dyes, contained in the hair dye composition.

The physiologically acceptable medium is preferably a solubilizing medium for the oxyethylene polymer(s) useful according to the invention and having a bacteriostatic property. It generally comprises a solvent or a mixture of solvents of the oxyethylene polymer(s).

Amongst the solvents suited for formulating the compositions according to the invention, one can mention water, alcohols and more particularly, ($C_1$–$C_6$) lower alkanols such as ethanol and isopropanol, benzyl alcohol and alkanediols such as ethylene glycol, propylene glycol and pentane diol, ethers, esters (in particular acetates), dimethylsulfoxide (DMSO), N-methylpyrrolidone (NMP), ketones (in particular acetone and mixtures thereof).

The physiologically acceptable medium preferably comprises water, particularly distilled or permuted water or a water/alcohol mixture, in particular water/ethanol.

The alcohol amount in the water/alcohol mixture may account for up to 80% in volume, preferably 70% in volume of the water/alcohol mixture.

Advantageously, the water/alcohol mixture is a water/ethanol mixture, where ethanol accounts for 70% in volume of the water/ethanol mixture.

The anti-penetration compositions for pre-treating hair according to the invention may include any conventional cosmetic builder, in a usual proportion, which does not adversely affect the required properties.

As a builder, one can more particularly mention conventional gelling and/or thickening agents, anionic, non ionic, cationic or amphoteric surfactants, pro-penetrating agents, emulsifiers, perfumes, preservatives, fillers, sunscreens, proteins, vitamins, provitamins, anionic, non ionic, cationic or amphoteric non fixing polymers, hydrating agents, emollients, softening agents, mineral, vegetable or synthetic oils, hydrophilic or lipophilic agents such as ceramids and pseudoceramides, anti-foaming agents, antiperspirant agents, anti-free radical agents, bactericides, sequestrants, anti-dandruff agents, alkalinizing agents, volatile or non volatile silicones, linear or cyclic, modified or not, polyols, and any other additive conventionally used in cosmetic compositions intended to be applied on the hair.

The amounts of such various builders are those conventionally used in the considered field.

The compositions according to the invention may be applied on the hair scalp, as well as on the hair, whether dry or wet, but are preferably used in a non rinsed mode, that is the compositions are applied on the hair scalp, as well as on the hair (as a pre-treatment), then they are allowed to rest for a few minutes or more before dyeing. But it is also possible to use the compositions according to the invention in a rinsed mode.

The compositions according to the invention may have all the forms appropriate for a topic application, including, in the form of solutions of the lotion or serum type; in the form of aqueous gels; in the form of emulsions obtained through dispersion of a fatty phase in an aqueous phase (H/E) or the opposite (E/H), having a more or less thick liquid consistency such as milks and more or less smooth creams; in the form of spray or aerosol; or in the form of a brush or a stick as well.

Such compositions are prepared according to the usual method.

Another object of the invention is also a method for limiting the penetration into the skin and/or the keratin fibres of a least one dye, preferably an oxidation dye, contained in a hair dyeing composition, characterized in that it comprises applying as a pre-treatment on the hair scalp and on the hair, before a hair dyeing process, using the hair colouring composition, a hair pre-treatment anti-penetration composition according to the invention.

Generally, the application time of the anti-penetration composition according to the invention on the hair scalp and on the hair ranges from five seconds to one hour, preferably from 1 to 10 minutes.

Generally, the oxidation dyes are all compounds or mixtures of compounds which, in the presence of an oxidizing agent, for example the oxygen from the air or oxygenated water, oxide resulting in a compound or a mixture of coloured compounds.

The oxidation dyes are generally selected amongst oxidation bases, coupling agents, orthodiphenols and the mixtures thereof.

The oxidation bases, of the para or ortho type, are compounds which are not dyes in themselves, but form a dye through an oxidative condensation process, either by themselves, or in the presence of a coupling or modifying agent. They have functional groups, either two amino groups or an amino group and a hydroxy group in a para or ortho position one relative to the other.

The nature of such oxidation bases is not critical. They may more particularly be selected amongst ortho- and para-phenylenediamines, double bases, ortho- and para-aminophenols, heterocyclic bases as well as the addition salts of all those compounds with an acid.

As examples of paraphenylenediamines, one can more particularly mention the paraphenylenediamines with the following chemical formula (4) and their addition salts with an acid:

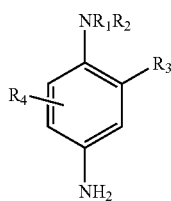

(4)

where:
$R_1$ represents a hydrogen atom, a $C_1$–$C_4$ alkyl, $C_1$–$C_4$ monohydroxyalkyl, $C_2$–$C_4$ polyhydroxyalkyl, ($C_1$–$C_4$) alkoxy($C_1$–$C_4$)alkyl, $C_1$–$C_4$ alkyl moiety substituted by a nitrogen, phenyl or 4'-aminophenyl group;

$R_2$ represents a hydrogen atom, a $C_1$–$C_4$ alkyl, $C_1$–$C_4$ monohydroxyalkyl or $C_2$–$C_4$ polyhydroxyalkyl, ($C_1$–$C_4$) alkoxy($C_1$–$C_4$)alkyl or $C_1$–$C_4$ alkyl moiety substituted by a nitrogen group;

$R_3$ represents a hydrogen atom, a halogen atom such as a chlorine atom, a $C_1$–$C_4$ alkyl, sulfo, carboxy, $C_1$–$C_4$ monohydroxyalkyl or $C_1$–$C_4$ hydroxyalkoxy, $C_1$–$C_4$ acetylaminoalkoxy, $C_1$–$C_4$ mesylaminoalkoxy or $C_1$–$C_4$ carbamoylaminoalkoxy moieties;

$R_4$ represents a hydrogen atom, a halogen atom, or a $C_1$–$C_4$ alkyl moiety;

$R_1$ and $R_2$ may also form with the nitrogen atom carrying them a 5 or 6 members nitrogen heterocycle optionally substituted by one or more alkyl, hydroxy or ureido groups.

Amongst the nitrogen groups with the above-mentioned formula (4), one can more particularly mention the amino, ($C_1$–$C_4$)monoalkylamino, ($C_1$–$C_4$)dialkylamino, ($C_1$–$C_4$) trialkyl amino, ($C_1$–$C_4$) monohydroxyalkylamino, imidazolinium and ammonium radicals.

Amongst the paraphenylenediamines of the above-mentioned formula (4), one can more particularly mention paraphenylenediamine, paratoluylenediamine, 2-chloro-paraphenylenediamine, 2,3-dimethyl-paraphenylenediamine, 2,6-dimethyl-paraphenylenediamine, 2,6-diethyl-paraphenylenediamine, 2,5-dimethyl-paraphenylenediamine, N,N-dimethyl-paraphenylenediamine, N,N-diethyl-paraphenylenediamine, N,N-dipropyl-paraphenylenediamine, 4-amino-N,N-diethyl-3-methyl-aniline, N,N-bis-(β-hydroxyethyl)-paraphenylenediamine, 4-N,N-bis-(β-hydroxyethyl)amino-2-methyl-aniline, 4-N,N-bis-(β-hydroxyethyl)-amino-2-chloro-aniline, 2-β-hydroxyethyl-paraphenylenediamine, 2-fluoro-paraphenylenediamine, 2-isopropyl-paraphenylenediamine, N-(β-hydroxypropyl)-paraphenylenediamine, 2-hydroxymethyl-paraphenylenediamine, N,N-dimethyl-3-methyl-paraphenylenediamine, N,N-(ethyl,β-hydroxyethyl)-paraphenylenediamine, N-(β,γ-dihydroxypropyl)-paraphenylenediamine, N-(4'-aminophenyl)-paraphenylenediamine, N-phenyl-paraphenylenediamine, 2-β-hydroxyethyloxy-paraphenylenediamine, 2-β-acetylaminoethyloxy-paraphenylenediamine, N-(β-methoxyethyl)-paraphenylenediamine, 2-methyl-1-N-β-hydroxyethyl-paraphenylenediamine, and their addition salts with an acid.

Amongst the paraphenylenediamines of the above-mentioned formula (4), are more particularly preferred paraphenylenediamine, paratoluylenediamine, 2-isopropyl-paraphenylenediamine, 2-β-hydroxyethyl-paraphenylenediamine, 2-β-hydroxyethyloxy-paraphenylenediamine, 2,6-dimethyl-paraphenylenediamine, 2,6-diethyl-paraphenylenediamine, 2,3-dimethyl-paraphenylenediamine, N,N-bis-(β-hydroxyethyl)paraphenylenediamine, 2-chloro-paraphenylenediamine, and their addition salts with an acid.

According to the invention, it is meant under double bases, the compounds comprising at least two aromatic rings on which are carried the amino and/or hydroxyl groups.

Amongst the double bases useful as oxidation bases in the dyeing compositions according to the invention, one can more particularly mention the compounds having the following formula (5) and their addition salts with an acid:

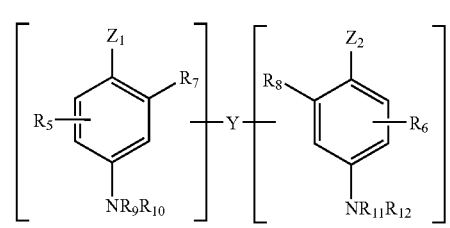

(5)

where:
$Z_1$ and $Z_2$, whether identical or different, represent a hydroxyl or —$NH_2$ moiety optionally substituted by a $C_1$–$C_4$ alkyl moiety or by a Y binding branch;

the Y binding branch represents an alkylene chain comprising 1 to 14 carbon atoms, linear or branched, able to be interrupted or ending with one or more nitrogen groups and/or by one or more heteroatoms such as oxygen, sulphur or nitrogen atoms, and optionally substituted by one ore more $C_1$–$C_6$ hydroxyl or alkoxy moieties;

$R_5$ and $R_6$ represent a hydrogen or a halogen atom, a $C_1$–$C_4$ alkyl, $C_1$–$C_4$ monohydroxyalkyl, $C_2$–$C_4$ polyhydroxyalkyl, $C_1$–$C_4$ aminoalkyl moiety or a Y binding branch;

$R_7$, $R_8$, $R_9$, $R_{10}$, $R_{11}$ and $R_{12}$, whether identical or different, represent a hydrogen atom, a Y binding branch or a $C_1$–$C_4$ alkyl moiety; on the condition that the compounds with formula (5) only have one Y binding branch per molecule.

Amongst the nitrogen groups of the above-mentioned formula (5), one can more particularly mention amino, ($C_1$–$C_4$)monoalkylamino, ($C_1$–$C_4$)dialkylamino, ($C_1$–$C_4$)trialkylamino, ($C_1$–$C_4$)monohydroxyalkyl amino, imidazolinium and ammonium moieties.

Amongst the double bases of the above-mentioned formulae (5), one can more particularly mention N,N'-bis-(β-hydroxyethyl) N,N'-bis-(4'-aminophenyl) 1,3-diamino propanol, N,N'-bis-(β-hydroxyethyl) N,N'-bis-(4'-aminophenyl)ethylenediamine, N,N'-bis-(4-aminophenyl) tetramethylenediamine, N,N'-bis-(β-hydroxyethyl) N,N'-bis-(4-aminophenyl) tetramethylenediamine, N,N'-bis-(4-methyl-aminophenyl) tetramethylenediamine, N,N'-bis-(ethyl) N,N'-bis-(4'-amino, 3'-methylphenyl) ethylenediamine, 1,8-bis-(2,5-diaminophenoxy)-3,5-dioxaoctane, and their addition salts with an acid.

Amongst those double bases of formula (5), N,N'-bis-(β-hydroxyethyl) N,N'-bis-(4'-aminophenyl) 1,3-diamino propanol, 1,8-bis-(2,5-diaminophenoxy)-3,5-dioxaoctane or one of their addition salts with an acid are particularly preferred.

Amongst the para-aminophenols, one can more particularly mention the para-aminophenols having the following formula (6), and their addition salts with an acid:

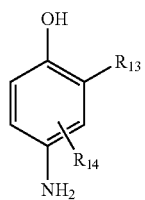

(6)

where:

$R_{13}$ represents a hydrogen atom, a halogen atom such as fluorine, a $C_1$–$C_4$ alkyl, $C_1$–$C_4$ monohydroxyalkyl, ($C_1$–$C_4$) alkoxy($C_1$–$C_4$)alkyl or $C_1$–$C_4$ aminoalkyl, or $C_1$–$C_4$ hydroxyalkyl($C_1$–$C_4$)aminoalkyl moiety; and $R_{14}$ represents a hydrogen atom or a halogen atom such as fluorine, a $C_1$–$C_4$ alkyl, $C_1$–$C_4$ monohydroxyalkyle, $C_2$–$C_4$ polyhydroxyalkyle, $C_1$–$C_4$ aminoalkyl, $C_1$–$C_4$ cyanoalkyl or ($C_1$–$C_4$)alkoxy($C_1$–$C_4$)alkyl moiety.

Amongst the para-aminophenols of the above-mentioned formula (6), one can more particularly mention para-aminophenol, 4-amino-3-methyl-phenol, 4-amino-3-fluoro-phenol, 4-amino-3-hydroxymethyl-phenol, 4-amino-2-methyl-phenol, 4-amino-2-hydroxymethyl-phenol, 4-amino-2-methoxymethyl-phenol, 4-amino-2-aminomethyl-phenol, 4-amino-2-(β-hydroxyethyl-aminomethyl)-phenol, and their addition salts with an acid.

The ortho-aminophenols useful as oxidation bases in the scope of the present invention, are more particularly selected amongst 2-amino-phenol, 2-amino-1-hydroxy-5-methyl-benzene, 2-amino-1-hydroxy-6-methyl-benzene, 5-acetamido-2-amino-phenol, and their addition salts with an acid.

Amongst the heterocyclic bases useful as oxidation bases in the dyeing compositions according to the invention, one can more particularly mention pyridine derivatives, pyrimidine derivatives, pyrazoline derivatives, and their addition salts with an acid.

Amongst the pyridine derivatives, one can more particularly mention the compounds as disclosed for example in Patents GB-1026978 and GB-1153196, such as 2,5-diamino-pyridine, 2-(4-methoxyphenyl)amino-3-amino-pyridine, 2,3-diamino-6-methoxy-pyridine, 2-(β-methoxyethyl)-amino-3-amino-6-methoxy pyridine, 3,4-diamino-pyridine, and their addition salts with an acid.

Amongst the pyrimidine derivatives, one can more particularly mention the compounds disclosed, for example, un the German Patent DE-2359399 or in Japanese Patents JP 88-169571 and JP-9110659 or in Patent Application WO 96/15765, such as 2,4,5,6-tetra-aminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine, and the pyrazolo-pyrimidine derivatives such as those mentioned in Patent Application FR-A-2 750 048 and amongst which are worth mentioning pyrazolo-[1,5-a]-pyrimidine-3,7-diamine; 2,5-dimethyl-pyrazolo-[1,5-a]-pyrimidine-3,7-diamine; pyrazolo-[1,5-a]-pyrimidine-3,5-diamine; 2,7-dimethyl-pyrazolo-[1,5-a]-pyrimidine-3,5-diamine; 3-amino-pyrazolo-[1,5-a]-pyrimidin-7-ol; 3-amino-pyrazolo-[1,5-a]-pyrimidin-5-ol; 2-(3-amino pyrazolo-[1,5-a]-pyrimidin-7-ylamino)-ethanol; 2-(7-amino-pyrazolo-[1,5-a]-pyrimidin-3-ylamino)-ethanol; 2-[(3-amino-pyrazolo[1,5-a]pyrimidin-7-yl)-(2-hydroxy-ethyl)-amino]-ethanol; 2-[(7-amino-pyrazolo[1,5-a]pyrimidin-3-yl)-(2-hydroxy-ethyl)-amino]-ethanol; 5,6-dimethyl-pyrazolo-[1,5-a]-pyrimidine-3,7-diamine; 2,6-dimethyl-pyrazolo-[1,5-a]-pyrimidine-3,7-diamine; 2,5,N7,N7-tetramethyl-pyrazolo-[1,5-a]-pyrimidine-3,7-diamine; 3-amino-5-methyl-7-imidazolylpropylamino pyrazolo-[1,5-a]-pyrimidine; and their addition salts and their tautomeric forms, when there is a tautomeric balance and their addition salts with an acid.

Amongst the pyrazolic derivates, one can more particularly mention those compounds disclosed in Patents DE-3843892, DE-4133957 and Patent Applications WO 94/08969, WO 94/08970, FR-A-2 733 749 and DE 19543988 such as 4,5-diamino-1-methyl-pyrazole, 3,4-diamino-pyrazole, 4,5-diamino-1-(4'-chlorobenzyl)-pyrazole, 4,5-diamino 1,3-dimethyl-pyrazole, 4,5-diamino-3-methyl-1-phenyl pyrazole, 4,5-diamino 1-methyl-3-phenyl-pyrazole, 4-amino-1,3-dimethyl-5-hydrazino-pyrazole, 1-benzyl-4,5-diamino-3-methyl-pyrazole, 4,5-diamino-3-tert-butyl-1-methyl pyrazole, 4,5-diamino-1-tert-butyl-3-methyl-pyrazole, 4,5-diamino-1-(β-hydroxyethyl)-3-methyl pyrazole, 4,5-diamino-1-(β-hydroxyethyl)-pyrazole, 4,5-diamino-1-ethyl-3-methyl-pyrazole, 4,5-diamino-1-ethyl-3-(4'-methoxyphenyl)-pyrazole, 4,5-diamino-1-ethyl-3-hydroxymethyl-pyrazole, 4,5-diamino-3-hydroxymethyl-1-methyl-pyrazole, 4,5-diamino-3-hydroxymethyl-1-isopropyl-pyrazole, 1,5-diamino-3-methyl-1-isopropyl-pyrazole, 4-amino-5-(2'-aminoethyl)amino-1,3-dimethyl-pyrazole, 3,4,5-triamino-pyrazole, 1-methyl-3,4,5-triamino-pyrazole, 3,5-diamino-1-methyl-4-methylamino-pyrazole, 3,5-diamino-4-(β-hydroxyethyl)amino-1-methyl-pyrazole, and their addition salts with an acid.

According to the present invention, the oxidation bases preferably represent approximately 0.005 to 12% in weight of the total weight of the composition and more preferably approximately 0.005 to 8% in weight of said weight.

Another oxidation class dyes comprises orthodiphenols. These are compounds comprising at least one aromatic ring, at least two consecutive carbons of which carry a hydroxyl group. Preferably, such an aromatic ring is a benzene ring or a condensed aromatic ring.

The aromatic ring may be a condensed aromatic ring optionally containing one or more heteroatoms, such as naphthalene, tetrahydronaphhtalene, indane, indene, anthracene, phenanthrene, indole, isoindole, indolin, isoindolin, benzofurane, dihydrobenzofurane, chromane, isochromane, chromene, isochromene, quinolein, tetrahydroquinolein and isoquinolein.

The preferred orthodiphenol oxidation dyes may be represented by the formula (7):

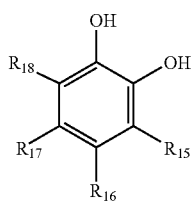

(7)

where the $R_{15}$ to $R_{18}$ substituents, identical or different, represent a hydrogen atom, a halogen, hydroxyl, carboxyl, alkyl carboxylate, optionally substituted amino, optionally substituted linear or branched alkyl, optionally substituted linear or branched alkenyl, optionally substituted cycloalkyl, alkoxy, alkoxyalkyl, alkoxyaryl radicals, the aryl group being optionally substituted, aryl, substituted aryl, an optionally substituted heterocyclic moiety, a moiety containing one or more silicon atoms, where two of the $R_{15}$ to $R_{18}$ substituents jointly form a saturated or an unsaturated ring optionally containing one or more heteroatoms and optionally condensed with one or more saturated or unsaturated rings optionally containing one or more heteroatoms.

The saturated or unsaturated rings, optionally condensed, may also be optionally substituted.

The alkyl moieties are generally $C_2$–$C_{10}$ alkyl moieties, preferably $C_1$–$C_6$ alkyl moieties, such as methyl, ethyl, propyl, butyl, pentyl and hexyl.

The alkoxy moieties are in general $C_1$–$C_{20}$ alkoxy moieties, such as methoxy, ethoxy, propoxy and butoxy.

The alkyl alkoxy moieties are preferably $(C_1$–$C_{20})$alkoxy $(C_1$–$C_{20})$ alkyl moieties such as methoxymethyl, ethoxymethyl, methoxyethyl, ethoxyethyle, etc.

The cycloalkyl moieties are in general $C_4$–$C_8$ cycloalkyl moieties, preferably cyclopentyl and cyclohexyl moieties. The cycloalkyl moieties may be substituted cycloalkyl moieties, in particular by alkyl, alkoxy, carboxylic acid, hydroxyl, amine and ketone groups.

The alkenyl groups are preferably $C_2$–$C_{20}$ moieties, such as ethylene, propylene, butylene, pentylene, methyl-2-propylene and decylene.

The moieties containing one or more silicon atoms are preferably polydimethylsiloxane, polydiphenylsiloxane, polydimethylphenylsiloxane, stearoxydimethicone moieties.

The heterocyclic moieties are in general moieties comprising one or more heteroatoms selected amongst O, N and S, preferably O or N, optionally substituted by one or more alkyl, alkoxy, carboxylic acid, hydroxyl, amine or ketone groups.

The preferred heterocyclic moieties include furyl, pyranyl, pyrrolyl imidazolyl, pyrazolyl, pyridyl, thienyl groups.

Still preferably, the heterocyclic groups are condensed groups such as benzofuranyl, chromenyl, xanthenyl, indolyl, isoindolyl, quinolyl, isoquinolyl, chromanyl, isochromanyl, indolinyl, isoindolinyl, coumarinyl, isocoumarinyl groups, such groups being optionally substituted, in particular by one or more OH groups.

The preferred orthodiphenol dyes are:
flavanols such as catechin and epichatechin gallate,
flavonols such as quercetin,
anthocyanidins such as peonidin,
anthocyanins, for example oenin,
hydroxybenzoates, such as for example gallic acid,
flavones such as luteolin,
iridoids such as oleuropein, such products being optionally osylated (for example glucosylated) and/or in the form of oligomers (procyanidins);
hydroxystilbenes, for example tetrahydroxy-3,3',4,5'-stilbene, optionally osylated (for example glucosylated);
3,4-dihydroxyphenylalanine and the derivates thereof;
2,3-dihydroxyphenylalanin and the derivates thereof;
4,5-dihydroxyphenylalanin and the derivates thereof;
4,5-dihydroxyindole and the derivates thereof;
5,6-dihydroxyindole and the derivates thereof;
6,7-dihydroxyindole and the derivates thereof;
2,3-dihydroxyindole and the derivates thereof;
dihydroxycinnamates such as cafeic acid and chlorogenic acid;
hydroxycoumarins;
hydroxyisocoumarins;
hydroxycoumarones;
hydroxyisocoumarones;
hydroxychalcones;
hydroxychromones;
anthocyanins;
quinones;
hydroxyxanthones; and
the mixtures thereof.

When the dyes are in the D and L forms, both forms can be used in the compositions according to the invention.

The particularly preferred orthodiphenols are 5,6-dihydroxyindole and 5,6-dihydroxyindole carboxylic acid.

The orthodiphenols such as previously defined can be contained in plant, fruit, citrus fruit, vegetable extracts and mixtures of such extracts.

Amongst plant extracts, one can mention rose and tea extracts.

Amongst fruit extracts, one can mention apple, grape (in particular grape seed) and banana extracts.

Amongst vegetable extracts, one can mention potato extract.

One can also use mixtures of plant and/or fruit extracts such as mixtures of apple and tea extracts and mixtures of grape and apple extracts.

Depending on the fruit parts being used, for example a pulp or grape seeds, the resulting colouration is different.

The orthodiphenols may be used together with the oxidation bases.

Another oxidation dye class is obtained by the coupling agents.

The coupling agents can be selected amongst those conventionally used in the oxidation dyeing field and including amongst meta-aminophenols, meta-phenylenediamines, metadiphenols, naphthols and heterocyclic coupling agents such as for example indole derivates, indolin derivates, sesamol and the derivates thereof, pyridine derivates, pyrazolotriazol derivates, pyrazolones, indazoles, benzimidazoles, benzothiazoles, benzoxazoles, 1,3-benzodioxoles, quinolins and their addition salts with an acid, such compounds being different from the orthodihydroxyl compounds of the invention.

Such coupling agents are more particularly selected amongst 2,4-diamino 1-(β-hydroxyethyloxy)benzene, 2-methyl 5-amino phenol, 5-N-(β-hydroxyethyl) amino 2-methyl phenol, 3-amino phenol, 1,3-dihydroxy benzene, 1,3-dihydroxy 2-methyl benzene, 4-chloro 1,3-dihydroxy benzene, 2-amino 4-(β-hydroxyethylamino) 1-methoxy benzene, 1,3-diamino benzene, 1,3-bis-(2,4-diaminophenoxy)propane, sesamol, 1-amino 2-methoxy 4,5-methylenedioxy benzene, α-naphtol,6-hydroxy indole, 4-hydroxy indole, 4-hydroxy N-methyl indole, 6-hydroxy indolin, 2,6-dihydroxy 4-methylpyridine, 1-H 3-methyl pyrazole 5-one, 1-phenyl 3-methyl pyrazole 5-one, 2-amino 3-hydroxypyridine, 3,6-dimethyl-pyrazolo-[3,2-c]-1,2,4-triazole, 2,6-dimethyl-pyrazolo-[1,5-b]-1,2,4-triazole and their addition salts with an acid.

Generally the coupling agent(s) preferably account for approximately 0.0001 to 15% in weight of the total weight of the ready-to-use dyeing composition and most preferably from approximately 0.001 to 10%.

The oxidation bases and the coupling agents comprise oxidation dyes. The addition salts with an acid of such oxidation dyes are more particularly selected amongst hydrochlorides, hydrobromides, sulphates and tartrates, lactates and acetates.

The oxidation dye amount in the dyeing composition should be sufficient to obtain a visible colouration. Such an amount may widely vary depending on the nature of the oxidation dyes and the intensity required for the dyeing operation.

In general, an appropriate colouration will be obtained when the dye amount is such that the dye content in the final dyeing composition is at least 0.1 micromol, preferably at least 1 micromol per millilitre of final composition.

Typically, the oxidation dye amount in the dyeing composition varies from 1 mM to 10 mM per litre and generally in the order of 5 mM per litre.

By varying the nature of the various oxidation dyes and their proportions in the composition, the final dyeing composition colour may change. A colour range is therefore obtained.

The hair dyeing compositions may contain, in addition to the oxidation dyes, one or more direct dyes, for example to modify the shades by enriching their glints. Such direct dyes may more particularly be selected amongst the nitrated, azoic or anthraquinon-type neutral, cationic or anionic dyes in the weight proportion of approximately 0.001 to 20% and preferably from 0.01 to 10% of the total weight of the composition.

The hair dyeing compositions may also contain an effective amount of at least one amino acid, in particular comprising at least one thiol (SH) group and preferably, a single thiol group, such amino acids being optionally under the form of hydrochlorides and/or at least one protein, in particular one peptide.

The preferred amino acids according to the invention are amino acids containing an amine position in an α position relative to a carboxylic acid function.

The preferred amino acids can be represented by the formula:

where —R is a divalent linear or branched hydrocarbon moiety, for example in $C_1$–$C_{10}$, preferably in $C_1$–$C_6$, such as a methylene, ethylene, butylene, ethylidene, propylidene moiety, a divalent saturated cyclic moiety, optionally substituted, for example in $C_4$–$C_8$, a divalent aromatic group, optionally substituted, such as a phenylene, tolylene, xylylene moiety.

Preferred amino acids for the compositions of the invention include cystein and the derivates thereof, in particulier L-cystein and L-cystein hydrochloride.

Proteins include gluthatione and the derivates thereof and soja protein.

The amino acid and/or protein and oxidation dye relative proportions in the compositions of the invention may widely vary depending on the desired colouration. Generally, the amino acid/oxidation dye molar ratio will vary from 0.001 to 50, preferably from 0.01 to 5, and more preferably from 0.05 to 2.5.

In general, the thiol group amino acid content in the final composition is at least 0.01 μmol per millilitre, preferably at least 0.1 μmol/ml.

By varying the nature of the dye precursors and amino acids in the composition and the amino acid and dye precursors relative proportion, a whole shade range may be obtained.

The compositions according to the invention can in addition comprise one or more enzymes.

The enzyme(s) present in the compositions according to the invention may be any enzymes having a propigmenting activity.

The propigmenting activity may be defined as the enzyme activity catalyzing for the oxidation of a substrate to lead to the formation of pigments.

The enzymes may more particularly be selected amongst pyranose oxidases, glucose oxidases, glycerol oxidases, lactate oxidases, pyruvate oxidases, uricases, cholin oxidases, sarcosin oxidases, bilirubin oxidases, laccases, tyrosinases, peroxidases, catalases, superoxidesdimutases and their mixtures, or amongst vegetable or animal extracts containing the above-mentioned enzymes, in the optional presence of a donor (or substrate) required for said enzymes to operate, such as for example L-tyrosin or L-DOPA.

The enzymes used according to the invention may be from animal, microbiological (bacterial, fungal or viral) or synthetic (obtained via chemical or biotechnological synthesis) nature.

The enzyme(s) may be used under pure or diluted crystalline form in a inert diluent for said enzyme.

As an example of uricases, one can more particularly mention uricase extracted from wild-boar liver, *Arthrobacter* globiformis uricase, as well as *Aspergillus flavus* uricase.

As an example of cholin oxidase sources, one can more particularly mention rat's liver, bacteria such as *Arthrobacter* globiformis, Achromobacter cholinophagum or *Alcaligenes*, and fungi such as Cylindrocarpon didynum.

As an example of sarcosin oxidase sources, one can more particularly mention bacteria such as *Arthrobacter* and in particular *Arthrobacter* ureafaciens and *Arthrobacter* globiformis, *Streptomyces, Bacillus, Pseudomonas, Corynebacterium* or *Alcaligenes* such as for example Alcaligenes denitrificans, and fungi such as Cylindrocarpon didynum.

As an example of bilirubin oxidase sources, one can more particularly mention rat's intestinal mucous membrane, bacteria such as *Myrothecium verucania, Myrothecium cinctum*, and *Myrothecium roridum*.

Amongst laccases from plant origin useful according to the invention, one can mention laccases produced by the plants achieving the chlorophyllous synthesis such as referred to in the patent application FR-A-2,694,018.

One can more particularly mention laccases extracted from Anacardiacees, Podocarpacees, Rosmarinus off., *Solanum tuberosum, Iris* sp., *Coffea* sp., *Daucus carrota, Vinca minor, Persea americana, Catharenthus roseus, Musa* sp., *Malus pumila, Gingko biloba*, and *Monotropa hypopithys* (sucepin).

Amongst laccases from microbial origin (including fungal), or obtained via biotechnology useful according to the invention, one can mention *Polyporus versicolor, Rhizoctonia praticola* and rhus vernicifera laccases such as disclosed for example in Patent Applications FR-A-2,112,549 and EP-A-504,005; lacases disclosed in Patent Applications WO95/07988, WO95/33836, WO95/33837, WO96/00290, WO97/19998 and WO97/19999, integrally incorporated into the present specification such as for example *Scytalidium, Polyporus pinsitus, Myceliophthora thermophila, Rhizoctonia solani, Pyricularia orizae* laccases, and the derivates thereof.

One will more preferably select the laccases from microbial origin or those obtained via biotechnology.

In a particularly preferred embodiment of the invention, the enzyme being used corresponds to tyrosinase (EC 1.14.18.1 nomenclature). Under tyrosinase, it is meant herein any enzyme having a tyrosinase activity, such an enzyme optionally having other enzyme activities. The tyrosinase activity may be defined as the enzyme activity catalyzing for the tyrosin oxidation to lead to the formation of the melanin precursor: Dopaquinon.

As an example of tyrosinase sources, one can more particularly mention potato, fungi, micro-organisms such as *Neurospora crassa*, etc.

The enzyme amount present in the final composition may widely vary, but usually ranges from $5.10^{-3}$ to 5 mg, preferably from $5.0^{-2}$ to 0.5 mg per millilitre of final composition.

The dyeing compositions may also contain other cosmetically acceptable builders, such as for example surfactants, thickening agents, penetration agents, perfumes, buffers, and various usual builders such as UV filters, waxes, volatile or non volatile, cyclic or linear or branched, organomodified (including by amine groups) or not silicones, preservatives, ceramids, pseudoceramids, plant, mineral or synthesis oils, vitamins or provitamins such as panthenol, opacifiers, reducing agents, emulsifiers, preservatives, fillers, sunscreens, proteins, anionic, non ionic, cationic or amphoteric fixing polymers, hydrating agents, emollients, softening agents, anti-foaming agents, antiperspirant agents, anti-free radical agents, fixing or non fixing polymers, bactericides, sequestrants, anti-dandruff agents, antioxidants, alkalinizing agents, polyols, and any other additive conventionally used in cosmetic compositions intended to be applied on the hair.

The surfactants may be selected amongst anionic, cationic, non ionic, amphoteric surfactants or the mixtures thereof, and preferably amongst non ionic surfactants.

Amongst such surfactants, one can mention alkylbenzenesulfonates, alkylnaphthalenesulfonates, sulphates, ether sulphates and fatty alcohol sulfonates, quaternary ammonium salts, such as trimethylcetylammonium bromide, cetylpyridinium bromide; optionally oxyethylenated fatty acid ethanolamides; polyoxyethylene acids, alcohols or amines, polyglycerol alcohols, polyoxyethylene or polyglycerol alkylphenols, as well as polyoxyethylene alkylsulphates.

The thickening agents that may be added in the dyeing compositions may be selected amongst sodium alginate, Arabic gum, cellulose derivates, acrylic acid polymers, xanthane gum. One can also use mineral thickening agents such as bentonite.

Organic UV filters may more particularly be selected from cinnamin derivates; dibenzoylmethane derivates; salicylic derivates; camphor derivates; triazine derivates such as those disclosed in Patent Applications U.S. Pat. No. 4,367, 390, EP-0,863,145, EP-0,517,104, EP-0,570,838, EP-0,796, 851, EP-0,775,698, EP-0,878,469, EP-0,933,376 et EP-0, 893,119; benzophenone derivates; β,β'-diphenylacrylate derivates; benzimidazole derivates; bis-benzoazolyl derivates such as those disclosed in Patents EP-0,669,323 and U.S. Pat. No. 2,463,264; bis-(hydroxyphenyl-benzotriazole) methylene derivates such as those disclosed in Patent Applications U.S. Pat. No. 5,237,071, U.S. Pat. No. 5,166,355, GB-2303549, DE-19726184 and EP-0,893, 119; p-aminobenzoic acid derivates; dimers derived from α-alkylstyrene such as disclosed in Patent Application DE-19855649; filter hydrocarbon polymers and filter silicones such as those disclosed more particularly in Patent Application WO 93/04665. One can also use pigments as well as nanopigments (average size of the primary particles: generally from 5 nm to 100 nm, preferably from 10 nm and 50 nm) of coated or non coated metal oxides such as for example nanopigments (amorphous or crystallized under rutile and/or anatase form) of titanium, iron, zinc, zirconium or cerium oxides which are all UV photoprotective agents well-known per se. Conventional coating agents are additionally alumina and/or aluminium stearate. Such metal oxide nanopigments, whether coated or not, are further disclosed in Patent Applications EP-0,518,772 and EP-0,518,773.

The dyeing compositions useful according to the invention may also comprise an effective amount of at least one oxidation dye and an effective amount of a system limiting the oxidation dye transcutaneous passage comprising a first component selected amongst salts and oxides of Mn(II) and/or Zn(II) and a second component selected amongst alkaline hydrogenocarbonates, alkaline earth hydrogenocarbonates and the mixtures thereof, the proportions of the first and the second components being such that:

$$\frac{[Mn(II)]}{[HCO_3]} \leq 1 \text{ with } [Mn(II)] \neq 0$$

$$\frac{[Zn(II)]}{[HCO_3]} \leq 1 \text{ with } [Zn(II)] \neq 0$$

$$\frac{[Mn(II) + Zn(II)]}{[HCO_3]} \leq 1 \text{ with } [Mn(II)] \text{ and } [Zn(II)] \neq 0$$

where [Mn(II)], [Zn(II)] and [HCO$_3$] respectively represent Mn(II), Zn(II) et HCO$_3$ molar concentrations in the composition.

Generally, the $$\frac{[Mn(II)]}{[HCO_3]}$$

ratio ranges from $10^{-5}$ to $10^{-1}$, preferably from $10^{-3}$ to $10^{-2}$ and more preferably, is in the order of $5.10^{-3}$.

In the case of Zn(II), the $$\frac{[Zn(II)]}{[HCO_3]}$$

ratio is in general of an order from 10 to 100 times than the ratio in the Mn(II) case.

Typically, such a ratio is $10^{-4}$ or more, and preferably in the order of $5.10^{-1}$.

In the case of a mixture of Mn(II) and Zn(II), the ratio generally ranges from $10^{-5}$ to $10^{-1}$, preferably $10^{-3}$ to $10^{-2}$, such a ratio being selected higher when the Zn(II) proportion in the mixture increases.

Generally, the Mn(II), Zn(II), or Mn(II)+Zn(II) molar concentration in the final composition ranges from $10^{-3}$ to 10 nM/l, preferably from $10^{-2}$ to 1 mM/l.

When only one or more Mn(II) salts or oxides is or are used, the Mn(II) molar concentration in the final composition typically ranges from $10^{-3}$ to $10^{-1}$ mM/l, preferably $10^{-2}$ to $10^{-1}$ mM/l.

Preferably, when only one or more Zn(II) salts or oxides is or are used, the Zn(II) concentration in the final composition ranges from $5.10^{-2}$ to 10 mM/l, more preferably from $5.10^{-1}$ to 1 mM/l.

Amongst the Mn(II) and Zn(II) salts appropriate for the present invention, one can mention chloride, fluoride, iodide, sulphate, phosphate, nitrate and perchlorate, carboxylic acid salts and the mixtures thereof.

By way of an example, one can mention manganese chloride, manganese carbonate (for example rhodochrosite), Mn(II) difluoride, Mn(II) acetate tetrahydrate, Mn(II) lactate trihydrate, Mn(II) phosphate, Mn(II) iodide, Mn(II) nitrate trihydrate, Mn(II) bromide and Mn(II) perchlorate tetrahydrate, and Mn(II) sulphate monohydrate.

The particularly preferred salts are $MnCl_2$ and $ZnCl_2$ and more particularly $MnCl_2$.

The carboxylic acid salts also include hydroxyl carboxylic acid salts such as gluconate.

Amongst the alkaline and earth alkaline hydrogenocarbonates, one can mention Na, K, Mg, Ca hydrogenocarbonates and the mixtures thereof, preferably Na hydrogenocarbonate.

Preferably, the compositions according to the invention are free from chélatants of Mn(II) and/or Zn(II) salts used, as such agents tend to inhibit the dye oxidation.

The following examples illustrate the present invention.

EXAMPLES

Dyeing experiments have been made on pig ear bristles, onto which as a pre-treatment (under the use condition) various compositions are applied each containing at least one oxyethylenated and/or oxypropylenated polymer, followed by a para-phenylenediamine based dye (PPD).

Such experiments are run ex vivo on a pig ear (from a slaughterhouse), as this represents a skin model close to the hair scalp and moreover has bristles representing the hair.

The pig ears have been mounted in diffusion cells in a static mode. Before the skin is mounted, the bristles are cut on a 5 mm length.

The PPD has been formulated in a carrier marketed by L'OREAL under the trade name Recital®. A dye consisting of a Recital® blend containing PPD and 20 oxygenated water volumes according to a volume ratio 1:1 has been prepared just before the application.

The aim of such experiments is to evaluate the oxyethylenated and/or oxypropylenated polymer ability to limit the PPD transcutaneous passage without interfering in the bristle dyeing process.

To this end, after successive applications of the pre-treatment composition and the dyeing composition onto the hair and the skin, the cutaneous absorption rate of the PPD, as well as the PPD rate in the bristles (as an index of the effect of the pre-treatment on the bristle dyeing process).

To facilitate the analysis, the radiomarked PPD [$^{14}$C]-PPD is used.

The following polymers have been tested alone or in blends:

Polymers useful according to the invention:
PEG-90, marketed by Fluka under the trade name Polyethylene glycol 4000 having an average molecular mass ranging from 3500 to 4500 g.mol$^{-1}$,
PEG 20000 marketed by Fluka under the trade name Polyethylene glycol 20000 having an average molecular mass ranging from 16,000 to 24,000 g.mol$^{-1}$,
Poloxamer 407 (CTFA name) marketed by BASF under the trade name Lutrol F-127®,
Polyethylene glycol copolymer comprising eight successive ethylene oxide and diisocyanate dicyclohexylmethane groups distributed in France by the Sederma company, under the trade name Polyolprepolymer-15® (or PP-15®).

Polymers tested by way of a comparison:
PEG-6 marketed by Fluka under the trade name Polyethylene glycol 300, having an average molecular mass ranging from 285 to 315 g.mol$^{-1}$,
PEG-45 marketed by Aldrich under the trade name Polyethylene glycol 2000 having an average molecular mass ranging from 1900 to 2200 g.mol$^{-1}$,
PEG-795 marketed by Fluka under the trade name Polyethylene glycol 35000 having an average molecular mass of about 35,000 g.mol$^{-1}$,
Poloxamer 188 (CTFA name) marketed by BASF under the trade name Lutrol F-68®,
Polypropylene glycol copolymer comprising twelve successive ethylene oxide and diisocyanate dicyclohexylmethane groups distributed in France by the Sederma company, under the trade name Polyolprepolymer-2® (or PP-2®).

Trials Running

Capillary pre-treatment compositions are made based on at least one oxyethylenated and/or oxypropylenated polymer by solubilizing the polymer(s) in ethanol (70% vol).

The pre-treatment compositions are then applied on pig ears, with a rate of 20 mg/cm$^2$ for 10 minutes. After drying (a polymeric "film" being then formed), the hair dye containing the [$^{14}$C]-PPD formulated in the Recital® carrier is then applied for 30 minutes, followed by a thorough washing operation simulating the after dyeing shampoo.

After a 24 hour period following the dye application, the [$^{14}$C]-PPD and/or the [$^{14}$C]-derivate rate is analyzed in the receiving liquid or in the skin including the bristles (5 bristles, all the bristles).

The application of the dye without any pre-treatment is used as a control.

The hair pre-treatment results are then evaluated compared to the results obtained without any pre-treatment, through quantifying two effects:

the anti-penetration effect, which evaluates the cutaneous absorption rate of the PPD and the derivates thereof, and the bristle effect, which evaluates the penetrating rate of the PPD and the derivates thereof into the bristles.

The bristle effect is an indicator of the influence of the pre-treatment on the penetration of an oxidation dye in the bristles (or the hair). An anti-penetration agent is therefore looked for which does not influence the dye penetration into the bristles (or the hair), that is which does not interact with the dyeing process.

It should consequently be of interest if applying the hair pre-treatment composition before the dyeing process would have an anti-penetration effect without having any bristle effect.

The bristle effect, expressed as a percentage, corresponds to the difference between the [$^{14}$C]-PPD and/or [$^{14}$C]-derivate amounts found in 5 bristles after a dyeing operation performed without any pre-treatment (control) and those found after the same dyeing process but run with a pre-treatment.

For both effects (antipenetration and bristles), a negative percentage shows a decrease of the rate found in the analysis compartment, whereas a positive percentage shows an increase of such a rate.

The anti-penetration effect is considered significant if, after a pre-treatment, the [$^{14}$C]-PPD and/or [$^{14}$C]-derivate amount found in the assembly formed by the stratum corneum, the malpighie epidermis, the dermis and the receiving liquid (referred to hereunder as "total skin+LR") has decreased by more than 25% compared to the same dyeing process without any pre-treatment. The anti-penetration effect is considered important if the [$^{14}$C]-PPD and/or [$^{14}$C]-derivate amount in the "total skin+LR" assembly has decreased by more than 50% compared to the non treated skin (control).

Therefore, the following indications will be used:

the "0" sign shows the experiments which do not show any significant anti-penetration effect, the "−" sign shows the experiments which show a pro-penetrating effect, i.e. the experiments for which the pre-treatment has increased the [$^{14}$C]-PPD and/or [$^{14}$C]-derivate amount found in the "total skin+LR" assembly, the "+" sign shows the experiments which show a significant anti-penetration effect, and the "++" sign shows the experiments showing an important anti-penetration effect.

Le pre-treatment is considered as non interfering with the dyeing process if the [$^{14}$C]-PPD and/or [$^{14}$C]-derivate amount found in 5 bristles has not been changed by ±25% compared to the same dyeing process without any pre-treatment. The bristle effect is considered significant if, after treatment, the [$^{14}$C]-PPD and/or [$^{14}$C]-derivate amount found in 5 bristles has increased or decreased by more than 25% compared to the same dyeing process without pre-treatment. The bristle effect is considered as important if, after treatment, the [$^{14}$C]-PPD and/or [$^{14}$C]-derivate amount found in 5 bristles has increased or decreased by more than 50% compared to the same dyeing process without pre-treatment.

The pre-treatment is considered as preventing the bristle colouring if, after treatment, the [$^{14}$C]-PPD and/or [$^{14}$C]-derivate amount found in 5 bristles has decreased by more than 25% compared to the same dyeing process without pre-treatment.

The following indications will be used:

the "0" sign shows the experiments which do not show any bristle effect, the "−" sign shows the experiments which show a bristle effect preventing the colouration, the "+" sign shows the experiments showing a significant bristle effect, and the "++" sign shows the experiments showing an important bristle effect.

Comparative Example

By way of a comparison, an experiment has been run for dyeing pig ear bristles, on which is applied, as a pre-treatment before dyeing, an ethanol solution (70% in vol.).

These experiment results (evaluation of the anti-penetration and the bristle effects) of such a trial are presented in the table hereinafter:

TABLE 1

| | Anti-penetration effect | Bristle effect |
|---|---|---|
| 70% volume ethanol solution (carrier) | − | + |

The results of these trials show that a 70% vol. ethanol solution leads to an increase of the [$^{14}$C]-PPD and/or [$^{14}$C]-derivate amount found in the "total skin+LR" assembly and to the occurrence of a significant bristle effect.

Example 1

Dyeing trials of pig ear bristles have been conducted onto which, as a pre-treatment before dyeing, an alcohol solution has been applied containing 10% in weight of polyethylene glycol based on the total volume of the composition. The results (evaluation of the anti-penetration and the bristle effects) of these trials are represented in table 2 hereinafter.

TABLE 2

| Solution containing 10% in weight* of polyethylene glycol** | Theoretical molecular mass*** (g · mol$^{-1}$) | Molecular mass according to the supplier (g · mol$^{-1}$) | n** | Anti-penetration effect | Bristle effect |
|---|---|---|---|---|---|
| PEG-6 | 300 | 285–315 | 6.4 | 0 | 0 |
| PEG-45 | 2000 | 1900–2200 | 45 | 0 | 0 |

TABLE 2-continued

| Solution containing 10% in weight* of polyethylene glycol** | Theoretical molecular mass*** (g · mol$^{-1}$) | Molecular mass according to the supplier (g · mol$^{-1}$) | n** | Anti-penetration effect | Bristle effect |
|---|---|---|---|---|---|
| PEG-90 | 4000 | 3500–4500 | 90.5 | + | 0 |
| PEG-454 | 20,000 | 16,000–24,000 | 454.1 | + | 0 |
| PEG-795 | 35,000 | ~35,000 | 795 | 0 | ++ |

*The percentages are expressed in weight based on the total volume of the composition.
**Number of ethylene oxide groups in a polyethylene glycol having the formula (1):
H[(OCH$_2$CH$_2$)$_n$OH (1)
***Calculated from the equation Mth = 18 + 44 × n The results represented in table 2 show that the compositions containing 10% in weight of PEG-90 and those containing 10% in weight of PEG-454 are compositions according to the invention, as the application, as a pre-treatment, of such compositions leads to an anti-penetration effect. Such compositions are, in addition, the preferred compositions according to the invention, as they further lead to the absence of the bristle effect.

The PEG-6, PEG-45 or PEG-795 based compositions are not in accordance with the invention as the application of such compositions as a pre-treatment does not lead to an anti-penetration effect.

Example 2

Dyeing trials have been conducted on pig ear bristles onto which, as a pre-treatment before dyeing, has been applied an alcohol solution containing 20% in weight of polyethylene glycol-90 based on the total volume of the composition.

The results of these trials (evaluation of the anti-penetration and the bristle effects) are gathered in table 3 hereinafter.

TABLE 3

| Solution containing 20% in weight* of polyethylene glycol** | Average molecular mass according to the supplier (in g · mol$^{-1}$) | Theoretical molecular mass*** (in g · mol$^{-1}$) | n** | Anti-penetration effect | Bristle effect |
|---|---|---|---|---|---|
| PEG-90 | 3500–4500 | 4000 | 90 | + | − |

*The percentages are expressed in weight based on the total volume of the composition.
**Number of ethylene oxide groups in a polyethylene glycol having the formula (1):
H(OCH$_2$CH$_2$)$_n$ OH (1)
***Calculated from the equation Mth = 18 + 44 × n The results represented in table 2 show that the compositions comprising 20% in weight of PEG-90 lead to an anti-penetration effect. Such compositions are therefore in accordance with the invention. However these are not the preferred compositions as the application, as a pre-treatment, of such compositions leads to the occurrence of a bristle effect preventing the colouration.

Example 3

Dyeing trials have been conducted on pig ear bristles onto which, as a pre-treatment before dyeing, has been applied an alcohol solution containing 5% in weight of PEG-90 based on the total volume of the composition. The results of these trials (evaluation of the anti-penetration and the bristle effects) are gathered in table 4 hereinafter.

TABLE 4

| Solution containing 5% in weight* of polyethylene glycol | Anti-penetration effect | Bristle effect |
|---|---|---|
| PEG-90* | 0 | 0 |

*The concentrations are weight percentages based on the total volume of the composition.

The results given in table 3 show that a composition containing 5% in weight of PEG 4000 is not in accordance with the invention, as the application of such a composition as a pre-treatment does not lead to an anti-penetration effect.

Example 4

Dyeing trials have been conducted on pig ear bristles onto which, as a pre-treatment before dyeing, has been applied an alcohol solution containing 10% in weight, based on the total volume of the composition, of polymers based on ethylene oxide and propylene oxide blocks (Poloxamer 407® and Poloxamer 188®. The results (evaluation of the anti-penetration and the bristle effects) of such trials are gathered in table 5.

TABLE 5

| Solution containing 10% in weight* of ethylene oxide and propylene oxide block polymers** | x** | y** | Anti-penetration effect | Bristle effect |
|---|---|---|---|---|
| Poloxamer 407 ® | 98 | 67 | + | ++ |
| Poloxamer 188 ® | 75 | 30 | 0 | 0 |

*The percentages are expressed in weight based on the total volume of the composition.
**x and y represent respectively the number of ethylene oxide groups and the number of propylene oxide groups in the block polymers having formula 2:

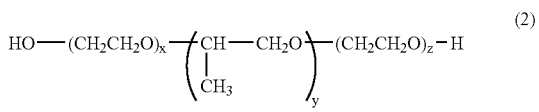

(2)

The results given in table 5 show that the application, as a pre-treatment of a Poloxamer 407® polymer based composition exhibits an anti-penetration effect, whereas the application, as a pre-treatment, of a Poloxamer 188® polymer based composition does not exhibit such an effect.

Consequently, the composition containing 10% in weight of Poloxamer 407® is indeed a composition according to the invention. However, as applying, as a pre-treatment, such a composition exhibits an important bristle effect, such a composition is not a preferred composition according to the invention.

Finally, a composition containing 10% in weight of Poloxamer 188® is not a composition according to the invention.

Example 5

Two dyeing trials have been conducted on pig ear bristles onto which, as a pre-treatment before dyeing, has been applied an alcohol solution of a polyethylene glycol and saturated methylene diphenyldiisocyanate (PP-15®) copolymer. The results of such trials (evaluation of the anti-penetration and the bristle effects) are presented in table 6.

TABLE 6

| Polymer | Concentration (%)* | Anti-penetration effect | Bristle effect |
|---|---|---|---|
| PP-15 ® | 10 | + | 0 |
|  | 20 | ++ | − |

*The concentrations are weight percentages based on the total volume total of the composition.

The results presented in table 6 show that when the dyeing operation is performed with a pre-treatment by means of a PP-15® solution, a significant bristle effect free anti-penetration effect is obtained when the PP-15® concentration accounts for 10% in weight based on the total volume of the composition, and with a bristle effect preventing the bristles from being dyed when the PP-15® concentration accounts for 20%.

Consequently, only the composition based on 10% in weight of PP-15® is in accordance with the invention.

Example 6

Similar trials to those of examples 1 to 5 have been conducted with a mixture of 5% in weight Poloxamer® and 5% in weight of PP-15®, with the results of such trials (evaluation of the anti-penetration and the bristle effects) being presented in table 7.

TABLE 7

|  | Anti-penetration effect | Bristle effect |
|---|---|---|
| Poloxamer 407 (5%)*/PP-15 (5%) mixture | + | 0 |

*the percentages are expressed in weight based on the total volume of the composition.

The results presented in table 7 show that a composition containing a mixture of 5% in weight of Poloxamer 407® and 5% in weight of PP-15® exhibits a significant bristle effect free anti-penetration effect.

Such a composition is consequently not only in accordance with the invention, but is also a preferred composition.

The invention claimed is:

1. A method for limiting the penetration into the scalp and/or the hair of at least one dye contained in a hair dyeing composition comprising applying on the scalp and/or on the hair, as a pre-treatment, before a hair dyeing process using the hair dyeing composition, a dye penetration limiting effective amount of an antipenetrating composition comprising, in a physiologically acceptable medium, an amount higher than 5% and lower than 20% in weight of the weight based on the total volume of the composition of at least one oxyethylenated polymer selected from the group consisting of:
   a) polyethylene glycols with the general formula (1):

$$H(OCH_2CH_2)_nOH \qquad (1)$$

where n is higher than 45 and lower than 795,
   b) block polymers with ethylene oxide and propylene oxide blocks, having the formula (2):

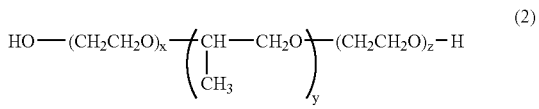

(2)

where
   x and z are such that at least one of x and z is higher than 75, and
   y is higher than 30,
   c) the polyethylene glycol copolymer comprising 8 successive ethylene oxide and dicyclohexylmethane diisocyanate groups having the formula (3):

$$HO[(C_2H_4O)_8-(C_{15}H_{24}N_2O_2)-(C_2H_4O)_8]_xH \qquad (3)$$

where x ranges from 1 to 4 such that the copolymer average molecular mass is 1800 g·mol$^{-1}$, and
   d) mixtures thereof.

2. The method according to claim 1 wherein the composition comprises a polyethylene glycol a) and the polyethylene glycol comprises 75 to 600 ethylene oxide groups per molecule.

3. The method according to claim 2, wherein the polyethylene glycol is selected from the group consisting of PEG-90, PEG-100, PEG-135, PEG-180, PEG-200, PEG-240, PEG-350 and PEG-454.

4. The method according to claim 1 wherein the composition comprises a block polymer with ethylene oxide and propylene oxide blocks b), having the formula 2), and wherein at least one of x and z is equal to or higher than 80 and y is higher than 45.

5. The method according to claim 4, wherein x and z are equal to 98 and y is equal to 67.

6. The method according to claim 1, wherein the physiologically acceptable medium is a solubilizing medium for the oxyethylenated polymer.

7. The method according to claim 1, wherein the physiologically acceptable medium comprises a solvent or a mixture of solvents for the oxyethylenated polymer.

8. The method according to claim 7, wherein the solvent is selected from the group consisting of water, alcohols, ethers, dimethylsulfoxide, N-methylpyrrolidone, acetones, and the mixtures thereof.

9. The method according to claim 8, wherein the solvent comprises at least one alcohol selected from the group consisting of alkanols, benzyl alcohol and alkanediols.

10. The method according to claim 9, wherein the alkanols are ($C_1$–$C_6$) lower alkanols.

11. The method according to claim 9, wherein the alkanediols are selected from the group consisting of ethylene glycol, propylene glycol and pentanediol.

12. The method according to claim 8, wherein the solvent is a water/alcohol mixture.

13. The method according to claim 12, wherein the alcohol accounts up to 80% in volume of the water/alcohol mixture.

14. The method according to claim 13, wherein the water/alcohol mixture is a water/ethanol mixture comprising 70% in volume of ethanol based on the weight of the water/ethanol mixture.

15. The method according to claim 1, wherein the composition further comprises conventional gellants, thickening agents, anionic, non ionic, cationic or amphoteric surfactants, propenetrating agents, emulsifiers, perfumes, preservatives, fillers, sunscreens, proteins, vitamins, provitamins, anionic, non ionic, cationic or amphoteric non fixing polymers, hydrating agents, emollients, softening agents, mineral, vegetable or synthetic oils, hydrophilic or lipophilic active ingredients, anti-foaming agents, antiperspirant agents, anti-free radical agents, bactericides, sequestrants, anti-dandruff agents, alkalinizing agents, volatile or non volatile, linear or cyclic, modified or not, silicones, polyols, or any other additive conventionally used in cosmetic compositions intended to be applied on the hair.

16. A method according to claim 1, wherein the application duration on the scalp and on the hair of the antipenetrating composition is from 5 seconds to one hour.

17. The method according to claim 1, wherein the at least one dye is an oxidation dye selected from the group consisting of oxidation bases, coupling agents, orthodiphenols and the mixture thereof.

18. A method according to claim 17, wherein the oxidation bases are selected from the group consisting of ortho- and para-phenylene diamines, double bases, ortho and para-aminophenols, heterocyclic bases and their additions salts with an acid.

19. A method according to claim 18, wherein the oxidation bases are selected from the group consisting of paraphenylenediamines having the formula (4):

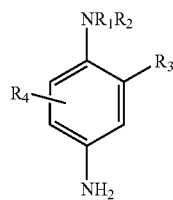

(4)

where:

$R_1$ represents a hydrogen atom, a $C_1$–$C_4$ alkyl moiety, a $C_1$–$C_4$ monohydroxyalkyl, $C_2$–$C_4$ polyhydroxyalkyl, ($C_1$–$C_4$)alkoxy($C_1$–$C_4$)alkyl, $C_1$–$C_4$ alkyl substituted by a nitrogen, phenyl or 4'-aminophenyl group;

$R_2$ represents a hydrogen atom, $C_1$–$C_4$ alkyl radical, a $C_1$–$C_4$ monohydroxyalkyl, $C_2$–$C_4$ polyhydroxyalkyl, ($C_1$–$C_4$)alkoxy($C_1$–$C_4$)alkyl or $C_1$–$C_4$ alkyl substituted by a nitrogen group;

$R_3$ represents a hydrogen atom, a halogen atom, a $C_1$–$C_4$ alkyl moiety, a sulfo, carboxy, a $C_1$–$C_4$ monohydroxyalkyl, $C_1$–$C_4$ hydroxyalkoxy, $C_1$–$C_4$ acetylaminoalkoxy, $C_1$–$C_4$ mesylaminoalkoxy or $C_1$–$C_4$ carbamoylaminoalkoxy group;

$R_4$ represents a hydrogen, halogen atom or a $C_1$–$C_4$ alkyl moiety;

$R_1$ and $R_2$ may also form with the nitrogen atom carrying them a 5 or 6 member nitrogen heteroring optionally substituted by one or more alkyl, hydroxy or ureido groups.

20. A method according to claim 19, wherein the paraphenylenediamines are selected from the group consisting of paraphenylenediamine, paratoluylenediamine, 2-isopropyl-paraphenylenediamine, 2-β-hydroxyethyl-paraphenylenediamine, 2,6-dimethyl-paraphenylenediamine, N,N-bis-(β-hydroxyethyl)-paraphenylenediamine, 2-chloro-paraphenylenediamine, and their addition salts with an acid.

21. A method according to claim 18, wherein the oxidation bases are double bases having the formula (5):

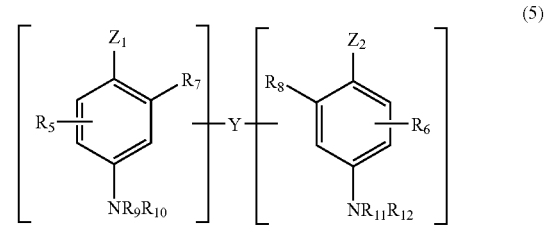

(5)

where:

$Z_1$ and $Z_2$, whether identical or different, represent a hydroxyl or -$NH_2$ moiety optionally substituted by a $C_1$–$C_4$ alkyl moiety or by a Y-binding branch;

the Y binding branch represents an alkylene chain comprising 1 to 14 carbon atoms, linear or branched, able to be interrupted or ending with one or more nitrogen groups and/or by one or more heteroatoms, and able to be substituted by one or more $C_1$–$C_6$ hydroxyl or alkoxy moieties;

$R_5$ and $R_6$ represent a hydrogen or a halogen atom, a $C_1$–$C_4$ alkyl, $C_1$–$C_4$ monohydroxyalkyl, $C_2$–$C_4$ polyhydroxyalkyl, $C_1$–$C_4$ aminoalkyl moiety or a Y binding branch;

$R_7$, $R_8$, $R_9$, $R_{10}$, $R_{11}$ and $R_{12}$, whether identical or different, represent a hydrogen atom, a Y binding branch or a $C_1$–$C_4$ alkyl moiety; on the condition that the compounds with formula (5) only have one Y binding branch per molecule.

22. A method according to claim 21, wherein the double bases are selected from the group consisting of N,N'-bis-(β-hydroxyethyl) N,N'-bis-(4'-aminophenyl) 1,3-diamino propanol, N,N'-bis-(β-hydroxyethyl) N,N'-bis-(4'-aminophenyl) ethylenediamine, N,N'-bis-(4-aminophenyl) tetramethylenediamine, N,N'-bis-(β-hydroxyethyl) N,N'-bis-(4-aminophenyl) tetramethylenediamine, N,N'-bis-(4-methyl-aminophenyl) tetramethylenediamine, N,N'-bis-(ethyl) N,N'-bis-(4'-amino, 3'-methyl) ethylenediamine, 1,8-bis-(2,5-diaminophenoxy)-3,5-dioxaoctane, and their addition salts with an acid.

23. A method according to claim 18, wherein the oxidation bases are para-aminophenols having the formula (6):

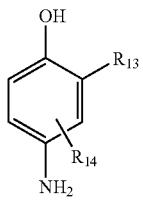

(6)

where:
R$_{13}$ represents a hydrogen atom, a halogen atom, a C$_1$–C$_4$ alkyl, C$_1$–C$_4$ monohydroxyalkyl, (C$_1$–C$_4$) alkoxy (C$_1$–C$_4$) alkyl, C$_1$–C$_4$ aminoalkyl, or C$_1$–C$_4$ hydroxyalkyl aminoalkyl(C$_1$–C$_4$) moiety; and
R$_{14}$ represents a hydrogen atom or a halogen atom, a C$_1$–C$_4$ alkyl, C$_1$–C$_4$ monohydroxyalkyl, C$_2$–C$_4$ polyhydroxyalkyl, C$_1$–C$_4$ aminoalkyl, C$_1$–C$_4$ cyanoalkyl or (C$_1$–C$_4$)alkoxy(C$_1$–C$_4$)alkyl moiety.

24. A method according to claim 23, wherein the para-aminophenols are selected from the group consisting of para-aminophenol, 4-amino-3-methyl-phenol, 4-amino-3-fluoro-phenol, 4-amino-3-hydroxymethyl-phenol, 4-amino-2-methyl-phenol, 4-amino-2-hydroxymethyl-phenol, 4-amino-2-methoxymethyl-phenol, 4-amino-2-aminomethyl-phenol, 4-amino-2-(β-hydroxyethyl-aminomethyl)-phenol, and their addition salts with an acid.

25. A method according to claim 18, wherein the oxidation bases are aminophenols selected from the group consisting of 2-amino-phenol, 2-amino-1-hydroxy-5-methyl-benzene, 2-amino-1-hydroxy-6-methyl-benzene, 5-acetamido-2-amino-phenol, and their addition salts thereof with an acid.

26. A method according to claim 18, wherein the oxidation bases are heterocyclic bases selected from the group consisting of pyridine derivates, pyrimidine derivates, pyrazoline derivates, and their addition salts with an acid.

27. A method according to claim 26, wherein the pyridine derivates are selected from the group consisting of 2,5-diamino-pyridine, 2-(4-methoxyphenyl) amino-3-amino-pyridine, 2,3-diamino-6-methoxy-pyridine, 2-(β-methoxyethyl) amino-3-amino-6-methoxy pyridine, and 3,4-diamino-pyridine.

28. A method according to claim 26, wherein the pyrimidine derivates are selected from the group consisting of 2,4,5,6-tetra-aminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine, pyrazolo-pyrimidine derivates, pyrazolo-[1,5-a]-pyrimidine-3,7-diamine; 2,5-dimethyl-pyrazolo-[1,5-a]-pyrimidine-3,7-diamine; pyrazolo-[1,5-a]-pyrimidine-3,5-diamine; 2,7-dimethyl-pyrazolo-[1,5-a]-pyrimidine-3,5-diamine; 3-amino-pyrazolo-[1,5-a]-pyrimidin-7-ol; 3-amino-pyrazolo-[1,5-a]-pyrimid- in-5-ol; 2-(3-amino pyrazolo-[1,5-a]-pyrimidin-7-ylamino)-ethanol; 2-(7-amino-pyrazolo-[1,5-a]-pyrimidin-3-amino)-ethanol; 2-[(3-amino-pyrazolo[1,5-a]pyrimidin-7-yl)-(2-hydroxy-ethyl)-amino]-ethanol; 2-[(7-amino-pyrazolo-[1,5-a]pyrimidin-3-yl)-(2-hydroxy-ethyl)-amino]-ethanol; 5,6-dimethyl-pyrazolo-[1,5-a]-pyrimidine-3,7-diamine; 2,6-dimethyl-pyrazolo-[1,5-a]-pyrimidine-3,7-diamine; 2,5,N7,N7-tetramethyl-pyrazolo-[1,5-a]-pyrimidine-3,7-diamine; 3-amino-5-methyl-7-imidazolylpropylamino pyrazolo-[1,5-a]-pyrimidine; and the addition salts thereof and their tautomeric forms, when there is a tautomeric balance.

29. A method according to claim 26, wherein the pyrazole derivates are selected from the group consisting of 4,5-diamino-1-methyl-pyrazole, 3,4-diamino-pyrazole, 4,5-diamino-1-(4'-chlorobenzyl)-pyrazole, 4,5-diamino 1,3-dimethyl-pyrazole, 4,5-diamino-3-methyl-1-phenyl pyrazole, 4,5-diamino 1-methyl-3-phenyl-pyrazole, 4-amino-1,3-dimethyl-5-hydrazino-pyrazole, 1-benzyl-4,5-diamino-3-methyl-pyrazole, 4,5-diamino-3-tert-butyl-1-methylpyrazole, 4,5-diamino-1-tert-butyl-3-methyl-pyrazole, 4,5-diamino-1-(β-hydroxyethyl)-3-methylpyrazole, 4,5-diamino-1-(β-hydroxyethyl)-pyrazole, 4,5-diamino-1-ethyl-3-methy-1-pyrazole, 4,5-diamino-1-ethyl-3-(4'-methoxyphenyl)-pyrazole, 4,5-diamino-1-ethyl-3-hydroxymethyl-pyrazole, 4,5-diamino-3-hydroxymethyl-1-methyl-pyrazole, 4,5-diamino-3-hydroxymethyl-1-isopropyl-pyrazole, 4,5-diamino-3-methyl-1-isopropyl-pyrazole, 4-amino-5-(2'-aminoethyl) amino-1,3-dimethyl-pyrazole, 4,5-triamino-pyrazole, 1-methyl-3,4,5-triamino-pyrazole, 3,5-diamino-1-methyl-4-methylamino-pyrazole, and 3,5-diamino-4-(β-hydroxyethyl)amino-1-methyl-pyrazole.

30. A method according to claim 18, wherein the oxidation base accounts for 0.0005 to 12% in weight of the total weight of the composition.

31. A method according to claim 17, wherein the orthodiphenols comprise a condensed benzene ring or an aromatic ring carrying at least two hydroxyl groups on two consecutive carbon atoms of the ring.

32. A method according to claim 31, wherein the orthodiphenols are compounds having the formula:

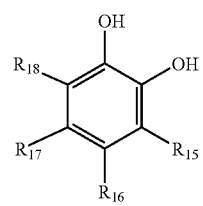

(7)

where the R$_{15}$ to R$_{18}$ substituents, identical or different, represent a hydrogen atom, a halogen, hydroxyl, carboxyl, alkyl carboxylate, optionally substituted amino moiety, optionally substituted linear or branched alkyl, optionally substituted linear or branched alkenyl, optionally substituted cycloalkyl, alkoxy, alkoxyalkyl, alkoxyaryl, the aryl group being optionally substituted, aryl, aryl substituted, an optionally substituted heterocyclic moiety, a moiety optionally containing one or more silicon atoms, where two of the R$_{15}$ to R$_{18}$ substituents form together a saturated or an unsaturated ring optionally containing one or more heteroatoms and optionally condensed with one or more saturated or unsaturated rings optionally containing one or more heteroatoms.

33. A method according to claim 31, wherein the orthodiphenols are selected from the group consisting of flavanols, flavonols, anthocyanidins, anthocyanines, hydroxybenzoates, flavones, iridoids, such compounds being optionally osylated and/or in the form of oligomers, optionally osylated hydroxystilbenes, 3,4-dihydroxyphenylalanine and the derivates thereof, 2,3-dihydroxyphenylalanine and the derivates thereof, 4,5-dihydroxyphenylalanine and the derivates thereof, 4,5-dihydroxyindole and the derivates thereof, 5,6-dihydroxyindole and the derivates thereof, 6,7-dihydroxyindole and the derivates thereof, 2,3-dihydroxyindole and the derivates thereof, dihydroxycinnamates, hydroxycoumarins, hydroxyisocoumarins, hydroxycoumarones, hydroxyisocoumarones, hydroxychalcones, hydroxychromones, anthocyanes, quinones, hydroxyxantones, and the mixtures of two or more of the previous compounds.

34. A method according to claim 33, wherein the orthodiphenols are selected from the group consisting of 5,6-dihydroxyindole and 5,6dihydroxyindole carboxylic acid.

35. A method according to claim 17, wherein the orthodiphenols are contained in plant, fruit or citrus fruit extracts, or mixtures of such extracts.

36. A method according to claim 35, wherein the orthodiphenols are contained in tea, grape, apple, banana, potato extracts, or mixtures of such extracts.

37. A method according to claim 17 wherein the coupling agents are selected from the group consisting of meta-aminophenols, meta-phenylenediamines, metadiphenols, naphthols, heterocyclic coupling agents, indole derivatives, indolin derivatives, sesamol and the derivates thereof, pyridine derivatives, pyrazolotriazole derivatives, pyrazolones, indazoles, benzimidazoles, benzothiazoles, benzoxazoles, 1,3-benzodioxoles, quinolins and their addition salts with an acid.

38. A method according to claim 37, wherein the coupling agents are selected from the group consisting of 2,4-diamino 1-(β-hydroxyethyloxy) benzene, 2-methyl 5-amino phenol, 5-N-(β-hydroxyethyl)amino 2-methyl phenol, 3-amino phenol, 1,3-dihydroxy benzene, 1,3-dihydroxy 2-methyl benzene, 4-chloro 1,3-dihydroxy benzene, 2-amino 4-(β-hydroxyethylamino) 1-methoxy benzene, 1,3-diamino benzene, 1,3-bis-(2,4-diaminophenoxy) propane, sesamol, 1-amino 2-methoxy 4,5-methylenedioxy benzene, α-naphthol, 6-hydroxy indole, 4-hydroxy indole, 4-hydroxy N-methyl indole, 6-hydroxy indoline, 2,6-dihydroxy 4-methyl pyridine, 1-H 3-methylpyrazole 5-one, 1-phenyl 3-methylpyrazole 5-one, 2-amino 3-hydroxypyridine, 3,6-dimethyl-pyrazolo-[3,2-c]-1,2,4-triazole, 2,6-dimethyl-pyrazolo-[1,5-b]-1,2,4-triazole and the addition salts thereof with an acid.

39. A method according to claim 37, wherein coupling agent(s) account(s) for 0.0001 to 15% in weight of the total weight of the composition.

40. A method according to claim 1, wherein the hair dyeing composition comprises one or more direct dyes.

41. A method according to claim 40 wherein direct dyes account for 0.001 to 20% in weight of the total weight of the composition.

42. A method according to claim 1, wherein the hair dyeing composition further comprises one or more amino acids and/or one or more proteins.

43. A method according to claim 42, wherein the amino acids comprise at least one thiol group and are selected from amino acids having an amine function in position a compared with a carboxylic acid function.

44. A method according to claim 42, wherein amino acid(s) is/are selected from cystein and the derivates thereof, and the proteins are selected from glutathione and the derivates thereof.

45. A method according to claim 42, wherein the molar ratio of the amino acid(s) and of the protein(s) to the other oxidation dyes varies from 0.001 to 50.

46. A method according to claim 1, wherein the hair dyeing composition further comprises an enzyme.

47. A method according to claim 46, wherein the enzyme is selected from the group consisting of pyranose oxydases glucose oxydases, glycerol oxydases, lactate oxydases, pyruvate oxidases, uricases, cholin oxidases, sarcosin oxidases, bilirubin oxydases, laccases, tyrosinases, peroxidases, catalases, superoxydesdimutases, plant or animal extracts containing the above-mentioned enzymes, and mixtures thereof.

48. A method according to claim 47, wherein the enzyme is a tyrosinase.

49. A method according to claim 47, wherein the hair dyeing composition comprises $5.10^{-3}$ to 5 mg of enzyme per millilitre of final composition.

50. A method according to claim 1, wherein the oxidation dye is present in an amount ranging from 1 mM to 10 mM per litre of composition.

51. A method according to claim 1, wherein the hair dyeing composition further comprises an effective amount of a system comprising a first component selected amongst the Mn(II) and/or Zn(II) salts and oxide and the mixtures thereof and a second component selected from alkaline hydrogenocarbonates, earth alkaline hydrogenocarbonates and the mixtures thereof, the proportions of the first and second component are such that:

$$\frac{[Mn(II)]}{[HCO_3]} \leq 1 \text{ with } [Mn(II)] \neq 0$$

$$\frac{[Zn(II)]}{[HCO_3]} \leq 1 \text{ with } [Zn(II)] \neq 0$$

$$\frac{[Mn(II) + Zn(II)]}{[HCO_3]} \leq 1 \text{ with } [Mn(II)] \text{ and } [Zn(II)] \neq 0$$

where [Mn(II)], [Zn(II)] and [HCO$_3$] represent respectively the Mn(II), Zn(II) molar concentrations and HCO$_3$ in the composition.

52. A method according to claim 51, wherein the ratio $$\frac{[Mn(II)]}{[HCO_3]}$$

varies from $10^{-5}$ to $10^{-1}$.

53. A method according to claim 51, wherein the ratio $$\frac{[Zn(II)]}{[HCO_3]}$$

varies from $10^{-4}$ to 1.

54. A method according to claim 51, wherein the ratio $$\frac{[Mn(II) + Zn(II)]}{[HCO_3]}$$

varies from $10^{-5}$ to $10^{-1}$.

55. A method according to claim 51, wherein the Mn(II) and Zn(II) salts are selected from the group consisting of chloride, fluoride, iodure, sulphate, phosphate, nitrate, perchlorate, carboxylic acid salts and the mixtures thereof.

56. A method according claim 51, wherein the Mn(II) and/or Zn(II) salt is a chloride.

57. A method according to any of claims 51 to 56, characterized in that the carboxylic acid salts are hydroxylated carboxylic acid salts.

58. A method according to claim 51, wherein the hydroxylated carboxylic acid salt is gluconate.

59. A method according to claim 51, wherein the hydrogenocarbonate is selected from the group consisting of sodium hydrogenocarbonate, potassium hydrogenocarbonate and the mixtures thereof.

60. The method according to claim 1, wherein the oxyethylenated polymer amount in the composition is lower than 15% in weight based on the total volume of the composition.

61. The method according to claim 1, wherein the oxyethylenated polymer amount in the composition is lower than 10% in weight based on the total volume of the composition.

62. The method according to claim 6, wherein the physiologically acceptable medium further comprises a bacteriological property.

63. The method according to claim 10, wherein the ($C_1$–$C_6$) lower alkanol is selected from the group consisting of ethanol and isopropanol.

64. The method according to claim 16, wherein the application duration on the scalp and on the hair of the antipenetrating composition is from 1 to 10 minutes.

65. The method according to claim 17, wherein the application duration on the scalp and on the hair of the antipenetrating composition is from 1 to 10 minutes.

66. The method according to claim 18, wherein the oxidation base accounts for 0.005 to 8% in weight of the total weight of the composition.

67. A method according to claim 37, wherein coupling agent(s) account(s) for 0.001 to 10% in weight of the total weight of the composition.

68. A method according to claim 39, wherein the hair dyeing composition comprises one or more direct dyes selected from the group consisting of nitrated, azoic or anthraquinonic neutral dyes, nitrated, azoic or anthraquinonic cationic dyes, and nitrated, azoic or anthraquinonic anionic dyes.

69. A method according to claim 40 wherein direct dyes account for 0.01 to 10% in weight of the total weight of the composition.

70. A method according to claim 42, wherein the molar ratio of the amino acid(s) and of the protein(s) to the other oxidation dyes varies from 0.05 to 2.5.

71. A method according to claim 47, wherein the hair dyeing composition comprises $5.10^{-2}$ to 0.5 mg of enzyme per millilitre of final composition.

* * * * *

UNITED STATES PATENT AND TRADEMARK OFFICE
CERTIFICATE OF CORRECTION

| | | |
|---|---|---|
| PATENT NO. | : 7,189,267 B2 | Page 1 of 1 |
| APPLICATION NO. | : 10/671499 | |
| DATED | : March 13, 2007 | |
| INVENTOR(S) | : Frank Dreher | |

It is certified that error appears in the above-identified patent and that said Letters Patent is hereby corrected as shown below:

Column 29, line 54, "a" should be --$\alpha$--.

Signed and Sealed this

Third Day of July, 2007

JON W. DUDAS
*Director of the United States Patent and Trademark Office*